(12) United States Patent
Hettel

(10) Patent No.: US 10,136,945 B2
(45) Date of Patent: Nov. 27, 2018

(54) ABLATION CATHETER WITH LIGHT-BASED CONTACT SENSORS

(71) Applicant: Biosense Webster (Israel) Ltd., Yokneam (IL)

(72) Inventor: Rowan Olund Hettel, Pasadena, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 458 days.

(21) Appl. No.: 14/964,209

(22) Filed: Dec. 9, 2015

(65) Prior Publication Data

US 2017/0164999 A1 Jun. 15, 2017

(51) Int. Cl.
*A61B 18/12* (2006.01)
*A61B 18/14* (2006.01)
(Continued)

(52) U.S. Cl.
CPC .......... *A61B 18/1492* (2013.01); *A61B 90/37* (2016.02); *A61B 90/30* (2016.02); *A61B 2017/00867* (2013.01); *A61B 2018/0022* (2013.01); *A61B 2018/00267* (2013.01); *A61B 2018/00351* (2013.01); *A61B 2018/00577* (2013.01); *A61B 2018/00642* (2013.01); *A61B 2018/00702* (2013.01); *A61B 2018/00904* (2013.01); *A61B 2018/1435* (2013.01); *A61B 2090/065* (2016.02); *A61B 2090/373* (2016.02)

(58) Field of Classification Search
CPC ...... A61B 18/1492; A61B 2017/00867; A61B 2018/0022; A61B 2018/00267; A61B 2018/00351; A61B 2018/00577; A61B 2018/00642; A61B 2018/00702; A61B 2018/00904; A61B 2018/1435; A61B 2090/065; A61B 2090/373

See application file for complete search history.

(56) References Cited

U.S. PATENT DOCUMENTS

| 5,391,199 A | 2/1995 | Ben-Haim |
| 6,239,724 B1 | 5/2001 | Doron et al. |

(Continued)

FOREIGN PATENT DOCUMENTS

| EP | 2397099 A1 | 12/2011 |
| WO | 96/05768 | 2/1996 |

(Continued)

OTHER PUBLICATIONS

European Search Report corresponding to European Patent Application No. 16202851.8 dated May 2, 2017, pp. 1-9.
U.S. Appl. No. 13/113,159, filed May 23, 2011.

*Primary Examiner* — Daniel Fowler
(74) *Attorney, Agent, or Firm* — Dergosits & Noah LLP; Todd A. Noah

(57) ABSTRACT

Devices and methods are disclosed for providing and using an ablation catheter. The catheter may include an expandable member having a plurality of electrodes, where each electrode is in association with at least one contact sensor and at least one light emitting element. Light is emitted in response to the contact of the contact sensor with the tissue to be ablated. A light sensor disposed centrally to the catheter gathers light emitted from the light emitting elements and sends a signal to a system controller for display.

20 Claims, 4 Drawing Sheets

(51) Int. Cl.
    *A61B 17/00*     (2006.01)
    *A61B 18/00*     (2006.01)
    *A61B 90/30*     (2016.01)
    *A61B 90/00*     (2016.01)

(56) References Cited

U.S. PATENT DOCUMENTS

| | | |
|---|---|---|
| 6,332,089 B1 | 12/2001 | Acker et al. |
| 6,427,089 B1 * | 7/2002 | Knowlton ............... A61B 18/18 607/101 |
| 6,468,260 B1 | 10/2002 | Bumbalough et al. |
| 6,484,118 B1 | 11/2002 | Govari |
| 6,500,167 B1 | 12/2002 | Webster, Jr. |
| 6,522,933 B2 | 2/2003 | Nguyen |
| 6,618,612 B1 | 9/2003 | Acker et al. |
| 6,690,963 B2 | 2/2004 | Ben-Haim et al. |
| 7,729,742 B2 | 6/2010 | Govari |
| 8,357,152 B2 | 1/2013 | Govari et al. |
| 8,617,087 B2 | 12/2013 | Schultz |
| 8,727,919 B1 | 5/2014 | Gentile |
| 9,050,105 B2 | 6/2015 | Govari et al. |
| 2004/0006333 A1 * | 1/2004 | Arnold .................. A61B 18/24 606/15 |
| 2004/0068178 A1 | 4/2004 | Govari |
| 2012/0253123 A1 | 10/2012 | Shimizu et al. |
| 2012/0314406 A1 | 12/2012 | Halliburton |
| 2014/0188035 A1 | 7/2014 | Ehrenreich et al. |
| 2014/0235135 A1 | 8/2014 | Henrik |

FOREIGN PATENT DOCUMENTS

| | | |
|---|---|---|
| WO | 01/03599 A2 | 1/2001 |
| WO | 2013/112844 A2 | 8/2013 |

* cited by examiner

ABLATION CATHETER WITH LIGHT-BASED CONTACT SENSORS

FIELD OF THE PRESENT DISCLOSURE

This disclosure relates generally to methods and devices for percutaneous medical treatment, and specifically to catheters, in particular, ablation catheters. More particularly, this disclosure relates to ablation catheter designs that have a light based sensing element for determining contact of ablation electrodes with the tissue to be treated.

BACKGROUND

Ablation of myocardial tissue is well known as a treatment for cardiac arrhythmias. In radio-frequency (RF) ablation, for example, a catheter is inserted into the heart and brought into contact with tissue at a target location. RF energy is then applied through an electrode on the catheter in order to create a lesion for the purpose of breaking arrhythmogenic current paths in the tissue. Recently, circumferential ablation of the ostia of the pulmonary veins has gained acceptance as a treatment for atrial arrhythmias, and particularly for atrial fibrillation.

As another example, a renal ablation procedure may involve the insertion of a catheter having multiple RF electrodes at its distal end into a renal artery in order to complete a circumferential or helical lesion in the artery in order to denervate the artery for the treatment of hypertension.

Contact with the tissue to be treated is critical to the success of the ablation procedure. Often, the practitioner is not certain that each of the electrodes is in contact with the tissue thereby causing delays in the procedure as well an ineffective result. In all of these procedures, whether using an ablation catheter or balloon, it is difficult to determine if each of the ablation electrodes has made contact with the tissue to be treated, especially in a multi-electrode device. Many times, the procedure may have to be repeated to make sure the ablation is complete. Repeated procedures increase the discomfort of the patient as well as an increase in the cost.

Some prior art devices may include a sensor for at or near a tip electrode to indicate contact with the treatment site. However, in a multi-electrode catheter or multi-electrode balloon catheter, contact sensors that readily indicate that contact has been made for each electrode are not available.

Accordingly, it would be desirable to provide an ablation catheter that has at least one sensor to easily detect if the electrode is in contact with the tissue. Likewise, it would be desirable to provide the practitioner with an easily readable indication of contact. As will be described in the following materials, this disclosure satisfies these and other needs.

SUMMARY

The present disclosure is directed to a catheter having an elongated body, an expandable element at a distal end of the elongated body, at least one electrode disposed on the expandable body, and at least one contact sensor disposed on the expandable element and adjacent to the at least one electrode. The elongate body further includes at least one light emitting element electrically connected to the contact sensor and a light sensor, the light sensor is configured to receive a light signal from the at least one light emitting element.

In one aspect, the at least one contact sensor is a flexible circuit formed by sputter coating on a flexible substrate.

In one aspect, the light emitting element is a plurality of RGB LED where each of the RGB LED corresponds to one of a plurality of electrodes. In another aspect the light emitting element is a white light emitting LED. In another aspect the light emitting element emits infrared light.

In one aspect, the contact sensor emits a light signal to the light sensor when in a closed position or in an open position.

In one aspect, the expandable member is a balloon where the light sensor is operably connected to a guidewire lumen.

In one aspect, the expandable member is a basket configuration having a plurality of spines and the light sensor is operably connected to a puller wire operably disposed along a central axis of the elongate body.

In one aspect, the expandable member comprises a helical shaped member where the light sensor is operably connected to a translation member operably disposed along a central axis of the elongate body. The helical member may be composed of a shape memory material This disclosure is also directed to a method for the ablation of a portion of tissue of a patient by an operator. The method includes inserting a catheter into the patient, the catheter including an elongated body, an expandable element positioned at a distal end of the elongated body, at least one electrode disposed on the expandable body, and at least one contact sensor disposed on the expandable element and adjacent to at least one electrode. The elongated body further includes at least one light emitting element electrically connected to the contact sensor, and a light sensor configured to receive a light signal from the at least one light emitting element. The method further includes connecting the catheter to a system controller capable of receiving signals from the light sensor and delivering power to the electrode, displaying an image based on the signals received from the light sensor, and controlling the power to the electrode to ablate tissue.

In one aspect, the method further includes positioning at least one electrode based on the displayed image based on the received light signals.

In one aspect, the method includes receiving signals from the light sensor from a plurality of RGB LED and adjusting the expandable member based on the displayed image. The method also includes estimating a degree of contact of the electrode based on the displayed image.

In one aspect, the received signals from the light sensor also include signals from a plurality of white light emitting LED.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form or omitted in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Figure 1:
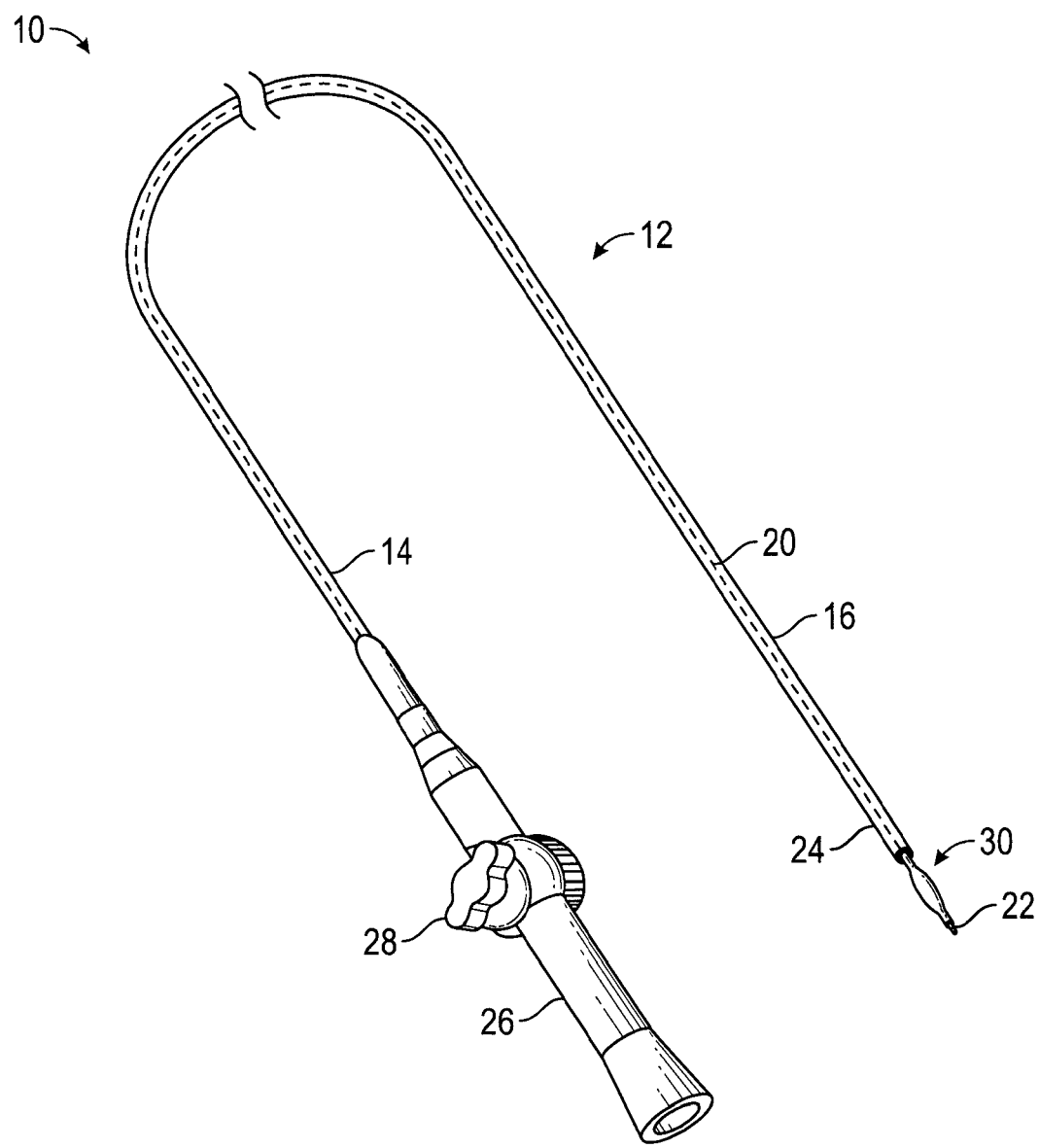
FIG. 1 is a perspective view of a catheter in accordance with an embodiment of the present invention.

As illustrated in FIG. 1, the present disclosure describes a medical device 10 for ablating target tissue. Medical device 10 includes an elongate body 12 such as a catheter. The elongate body 12 may define a proximal portion 14 and a distal portion 16 and may further include one or more lumens disposed within the elongate body 12 to provide mechanical, electrical, and/or fluid communication between the proximal portion of elongate body 12 and the distal portion of elongate body 12. For example, elongate body 12 may include an injection lumen defining a fluid flow path therethrough. In addition, elongate body 12 may include a guidewire lumen 20 for housing guide wire 22. Guidewire lumen 20 may be disposed within and/or extending along at least a portion of the elongate body 12 for over-the-wire or rapid exchange applications. In one embodiment, guidewire lumen 20 is a moveable lumen, as discussed in more detail below.

Catheter 10 may further include an outer sheath 24. Outer sheath 24 may be provided which is slidably positionable about at least a portion of the elongate body 12 of medical device 10. In another embodiment, outer sheath 24 may be stationary to constrain a longitudinally moveable ablation device.

Proximal of elongate body 12 is control handle 26 that allows an operator to maneuver the catheter, including by deflecting distal section 16 when a steerable embodiment is employed. For example, control handle 26 may include deflection knob 28 that is pivoted in a clockwise or counterclockwise direction for deflection in the respective direction. In other embodiments, other steerable designs may be employed, such as the control handles for manipulating multiple control wires as described, for example, in U.S. Pat. Nos. 6,468,260, 6,500,167, 6,522,933 and 8,617,087, the entire disclosures of which are incorporated herein by reference.

Elongate body 12 is flexible, i.e., bendable, but substantially non-compressible along its length and may be of any suitable construction and made of any suitable material. In one aspect, an outer wall made of polyurethane or PEBAX may have an imbedded braided mesh of stainless steel or the like, as is generally known in the art, to increase torsional stiffness of elongate body 12 so that, when the control handle 26 is rotated, the distal section 16 will rotate in a corresponding manner. Depending upon the intended use, the outer diameter of elongate body 12 may be approximately 8 french, and in some embodiments, may be 7 french. Likewise the thickness of the outer wall of elongate body 12 may be thin enough so that a central lumen may accommodate any desired wires, cables and/or tubes, as will be described in further detail below. The useful length of the catheter, i.e., that portion that can be inserted into the body may vary as desired. In exemplary embodiments, the useful length may range from about 110 cm to about 120 cm.

The medical device 10 of the present invention further includes an expandable element 30. Expandable element 30 may include a balloon (FIGS. 2 and 3) or other expandable structure such as a basket-shaped device (FIG. 4) or helical device (FIG. 5). As discussed in more detail below, each of the expandable elements 30 further includes a plurality of ablation electrodes, contact sensors and light emitters.

Figure 2:
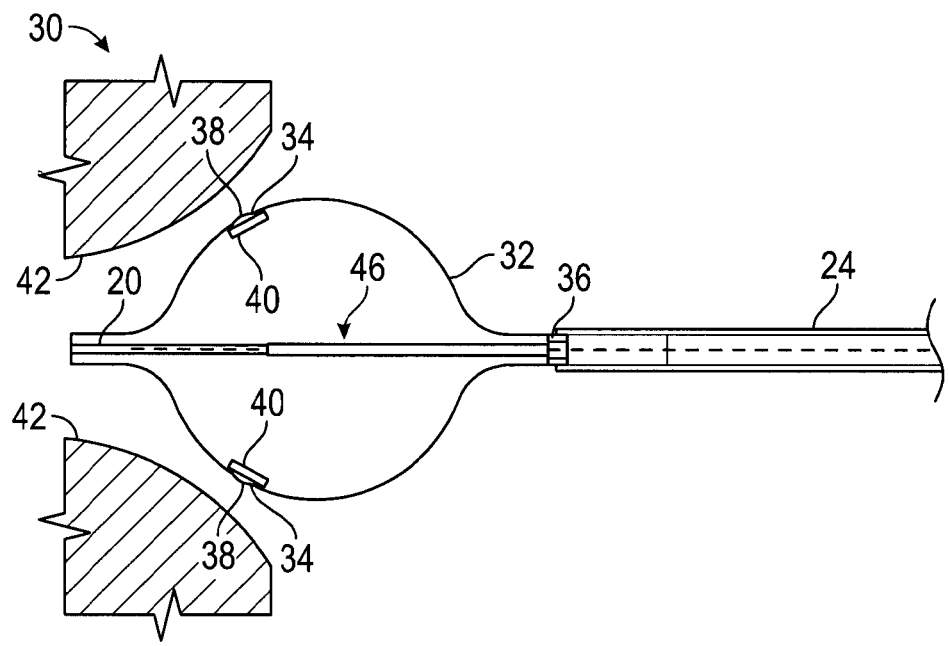
FIG. 2 is a cross section of an expandable element at the distal end of the catheter of FIG. 1 in accordance with an embodiment of the present invention.
Figure 3:
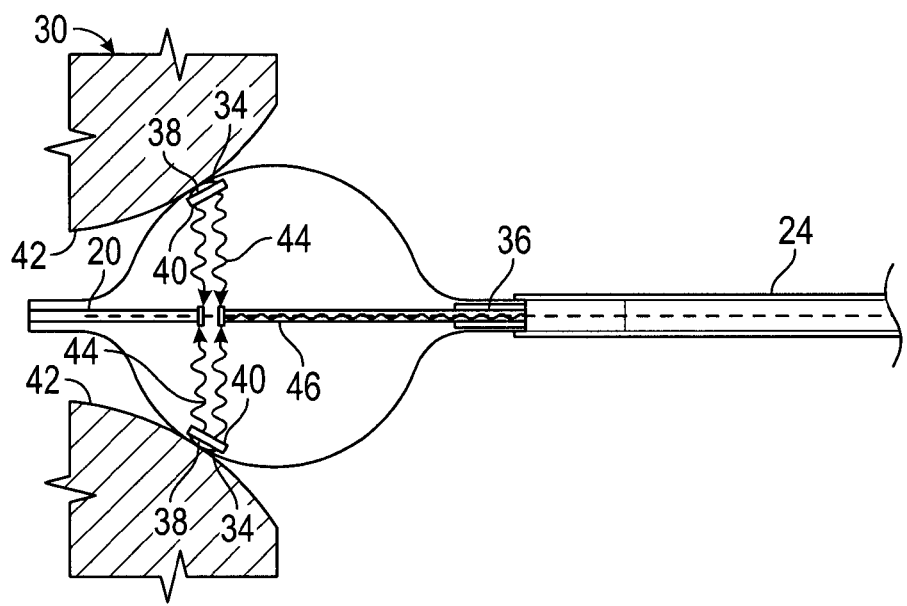
FIG. 3 is a cross section of an expandable element at the distal end of the catheter of FIG. 1 in accordance with an embodiment of the present invention.

Details regarding one embodiment of the expandable element 30 of catheter 10 are illustrated in FIGS. 2-3. Referring now to FIG. 2, expandable element 30 comprises an inflatable balloon 32. Balloon 32 may be a compliant or non-compliant balloon. In one embodiment, balloon 32 may have a generally spherical shape, as shown, or may have other shapes, such as disk shaped or donut shaped, or other profile to mimic the pulmonary vein ostia and the tissues extending therefrom. In one embodiment, balloon 32 is attached at its proximal end to a distal end of an inner catheter 36 and at its distal end to a distal portion of guidewire lumen 20. Balloon 32 further includes a plurality of electrodes 34 mounted on or embedded in its external surface. Electrodes 34 may be radiofrequency (RF) electrodes or electrical signal mapping electrodes. Electrode 34 may be made of any suitable electrically-conductive material, such as palladium, platinum, gold, iridium and combinations and alloys thereof, including, Pd/Pt (e.g., 80% Palladium/20% Platinum) and Pt/Ir (e.g., 90% Platinum/10% Iridium).

Expandable element 30 further includes a plurality of contact sensors 38. In one embodiment, each of the electrodes 34 has a corresponding contact sensor 38. Contact sensor 38 provides an indication to the practitioner that the electrode is in contact with the tissue 42 at the treatment site. In one embodiment, contact sensor 38 is a flexible circuit. In one embodiment, the flexible circuit is a thin-film circuit each of which is deposited on or bonded to the surface of balloon 32 by any method known in the art such as, for example, sputter coating, dipping or electrical deposition. In one embodiment, the method of manufacturing a flexible circuit contact sensor 38 comprises a polyimide material with a thin layer of copper and gold sputter coated or electroplated onto the polyimide layer. In another embodiment the flexible contact sensor comprises a nitinol material with deposited gold onto the nitinol layer. In another embodiment the flexible contact sensor comprises of a thin-film polymer substrate with gold directly deposited to the substrate. In this invention, the flexible circuit has an open configuration and a closed configuration. FIG. 2 illustrates the open configuration and FIG. 3 illustrates the closed configuration. In this embodiment, each contact sensor 38 further includes a light emitting element 40. In one embodiment, light emitting element 40 is a light emitting diode (LED). During the procedure, when the electrode 38 is not in contact with the tissue 42, the contact sensor remains in the open configuration. However, when electrode 38 makes contact with tissue 42 (FIG. 3), the circuit is closed allowing electricity to pass through the closed circuit to energize the light emitting element 40. Light, illustrated by wavy lines 44 (FIG. 3), emanating from the LED is detected by light sensor 46 disposed on an inner member of expandable element 30. In one embodiment, light sensor 46 is disposed on an outer surface of guidewire lumen 20. Light sensor 46 is electrically connected through appropriate wires to sensor module 224 (FIG. 7).

Light sensor 46 is capable of detecting light from a plurality of sources at the same time. In one embodiment, each electrode has a corresponding contact sensor 38 and LED 40. When each electrode is in contact with the target tissue, each LED is illuminated. In an embodiment, such as a balloon 32 configured to treat a pulmonary ostia, the device may have 10 to 20 electrodes for ablating the tissue in a circumferential pattern. In this embodiment, there would then be 10 to 20 LED emitting lights toward the sensor. Sensor module 224 may display to the practitioner which of the LEDs are lit to indicate contact, and which are not lit to indicate that contact is not present. In one embodiment, the LEDs are RGB LEDs, emitting either red, green or blue light. In this embodiment, the color that is detected and displayed (218) (see FIG. 6) to the practitioner may be configured to provide the level of contact. In one embodiment, the display of "Red" indicates no contact, while the display of "Blue" indicates full contact. The display of "Green" may indicate partial, but not complete, contact. In yet another embodiment, contact sensor 38 is initially in a closed configuration where the light emitting element 40 is emitting light toward sensor 46. When contact is made by the electrode 34, the contact sensor switches to an open configuration where the light is no longer emitted. In this embodiment, the absence of light displayed to the practitioner indicates complete contact with the tissue to be treated.

Figure 4:
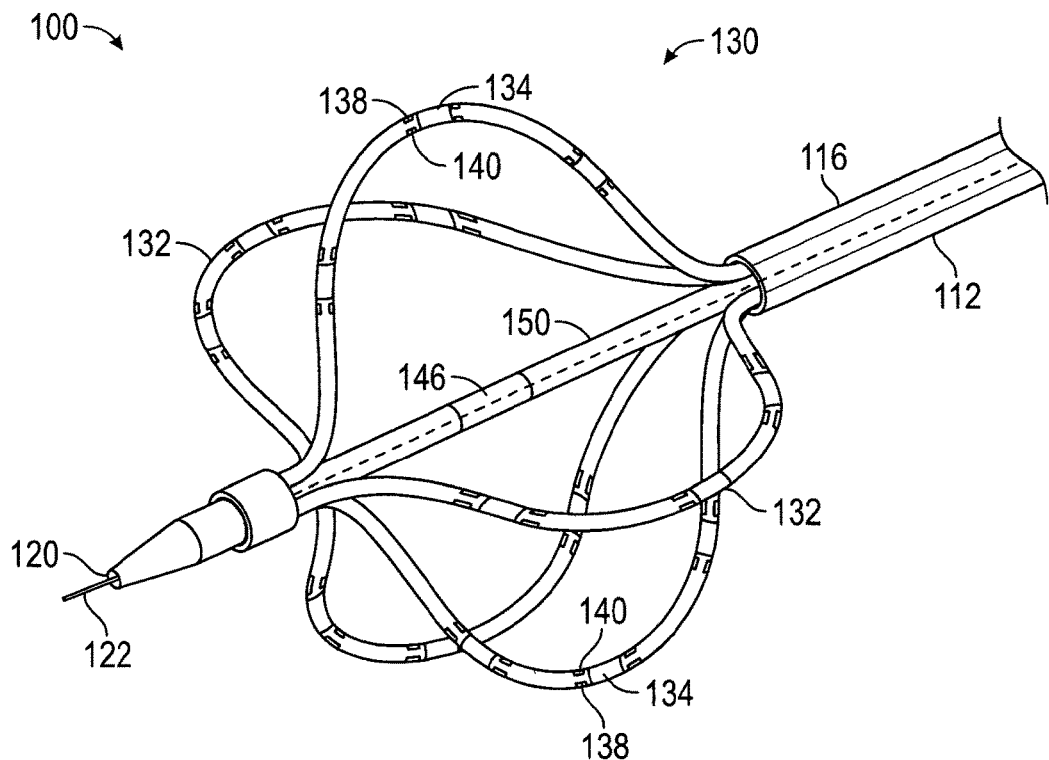
FIG. 4 is a perspective view of an expandable element, in accordance with another embodiment of the present invention.
Figure 5:
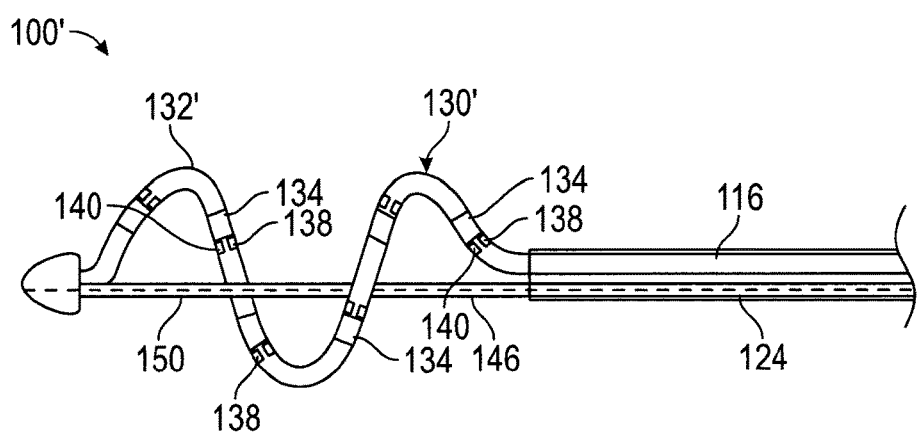
FIG. 5 is a perspective view of an expandable element, in accordance with another embodiment of the present invention.

Turning now to FIG. 4, illustrated is another embodiment of medical device 100 having a basket shaped expandable member 130. In this embodiment, expandable member 130 has a plurality of spines 132 each connected at its proximal end to a distal end 116 of elongate body 112 and at its distal end to a distal portion of a puller member 150. In one embodiment, each spine 132 is composed of a metallic wire having a non-conductive coating. In an example, spines 132 comprise a Nitinol™ wire core with a polyamide covering. In another example, spines 132 are composed of a Nitinol wire core with a PEBAX tube covering. In another example, spines 132 are composed of a braided polymer tube such as PEBAX or Pellethane that has a durometer that is sufficient enough to retain the basket shape when deployed. In another example, spines 132 are composed of a stainless steel core with any of the non-conductive coverings previously discussed.

In this embodiment, each spine 132 includes a plurality of electrodes 134, where each electrode is associated with a corresponding contact sensor 138 and light emitting element 140. In this embodiment, each electrode may be an ablation electrode or a mapping electrode as described above. In one embodiment, device 100 includes a mixture of ablation electrodes and mapping electrodes. Similar to the embodiment described above for FIGS. 2 and 3, each contact sensor is a flexible circuit having an open configuration and a closed configuration. In this embodiment, contact sensors 138 comprise flexible circuits that are manufactured using sputter coating, dipping or electro-deposition methods described above. In another embodiment, contact sensors 138 are not flexible circuits formed by thin film or deposition processes, but are formed using more traditional methods, as are known in the art. For example, direct wiring to contact sensors by hand as is typically done in EP diagnostic and therapeutic catheter assembly today. In all other aspects, the embodiment illustrated in FIG. 4 is similar to that illustrated in FIGS. 2 and 3. In one embodiment, light emitting elements 140 emit light toward a sensor 146 located on puller member 150 when the contact sensor is in a closed position. In another embodiment, light emitting elements 140 emit light towards light sensor 146 when in an open configuration. In each embodiment, light emitting element may be an LED emitting white light, or an LED emitting RGB light.

Turning now to FIG. 5, illustrated is another embodiment of a medical device 100' for ablating tissue. In this embodiment, medical device 100' includes a helically shaped expandable member 130'. Expandable member 130' is similar to that described above in FIG. 4, having similar electrodes 134, contact sensors 138 and light emitting elements 140. However, in this embodiment, expandable member 130' comprises a helically shaped spine 132' having electrodes and associated contact sensors disposed in a helical pattern along the length of spine 132'. In this embodiment, longitudinal movement of puller member 150' moves expandable member 130 from a closed configuration to an open helical configuration. In another embodiment, longitudinally retracting sheath 124' exposes expandable member 130' which, when exposed, forms the helical shape. In this embodiment, spine 132 is composed of a shape memory material such as, for example, Nitinol™ alloy and a non-conductive cover such as polyamide. As in the previous embodiment, contact sensors 138 and light emitting elements 140 indicate to the practitioner when the electrodes are in contact with the target tissue. As above, light emitting elements may be white light emitting LED or RGB light emitting LED. In use, this spine 132' will form a helical lesion pattern at the target tissue. In one example, the target tissue is a pulmonary vein. In another example, the target tissue is a renal artery. In both examples, practitioners have found that a helical pattern of lesions is preferable to a concentric circular pattern of lesions to avoid occlusion of the vessel.

In each of the above embodiment, medical device 10, 100 or 100' may include structures and conduits to accommodate electromagnetic position sensors that may be used in conjunction with a mapping system to aid visualization of the placement of the distal end of catheter 10 within a patient's anatomy and/or a force or contact sensing system. Details regarding such aspects may be found in U.S. Pat. Nos. 8,357,152 and 9,050,105, both of which are incorporated herein by reference in their entirety.

In comparison to conventional RF ablation catheters, the techniques of this disclosure represent notable benefits. Contact force catheters are capable of demonstrating contact with tissue but only at a tip and do not provide an indication as to how much of the electrode is in contact with tissue. Here, the contact sensors provide information as to which electrode is in contact and may provide an indication as to how much of the electrode is in contact using an appropriate light emitting element.

Figure 6:
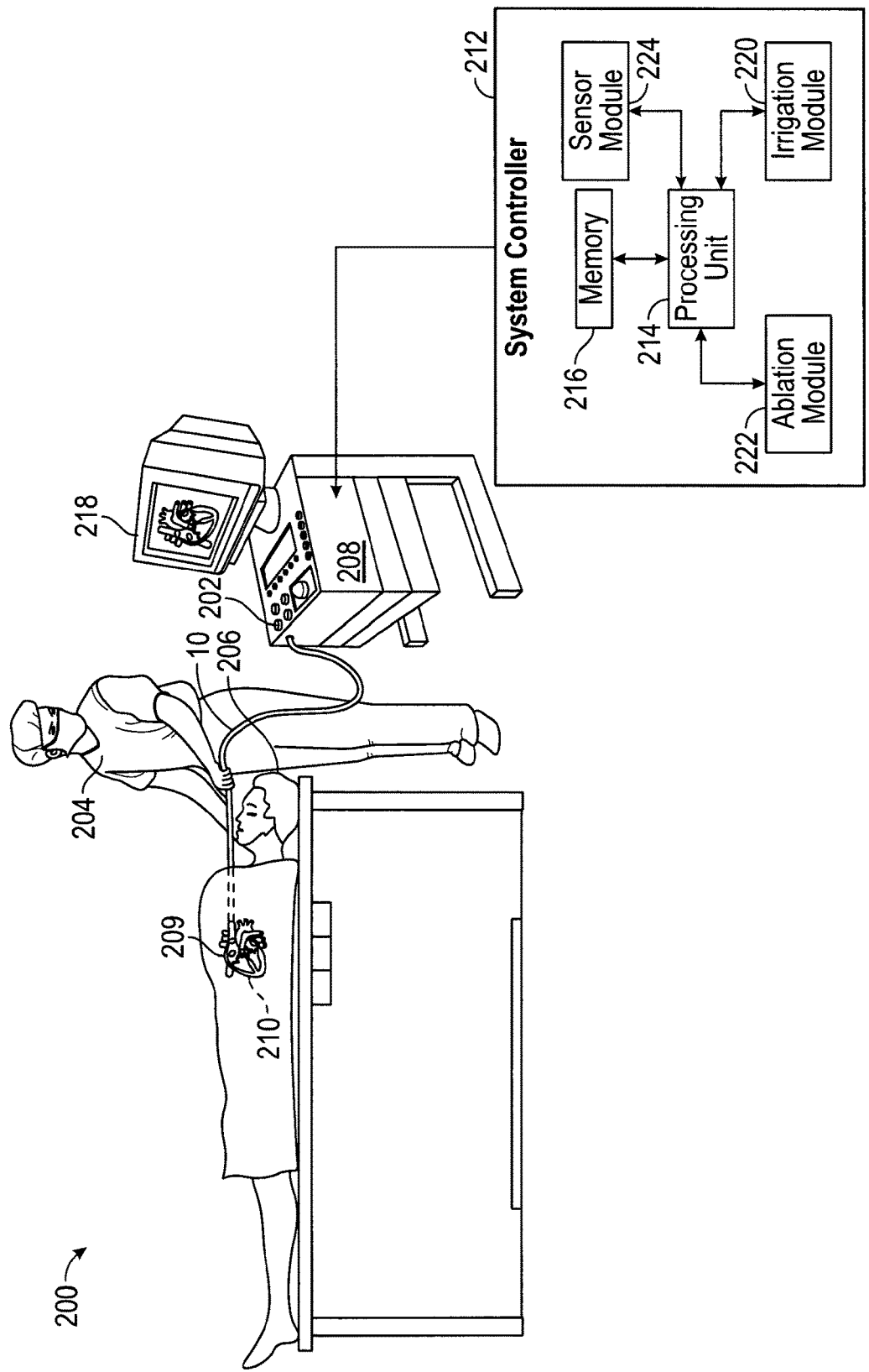
FIG. 6 is a schematic view of an ablation system in accordance with an embodiment of the present invention.

Use of catheter 10 in an ablation procedure may follow techniques known to those of skill in the art. FIG. 6 is a schematic, pictorial illustration of a system 200 for renal and/or cardiac catheterization and ablation, in accordance with an embodiment of the present invention. System 200 may be based, for example, on the CARTO™ mapping systems, produced by Biosense Webster Inc. (Diamond Bar, Calif.) and/or SmartAblate or nMarq RF generators. This system comprises an invasive probe in the form of catheter 10, 100 or 100' and a control and/or ablation console 202. An operator 204, such as a cardiologist, electrophysiologist or interventional radiologist, inserts ablation catheter 10, 100 or 100' into and through the body of a patient 206, such as through a femoral or radial access approach, so that a distal end of catheter 10, 100 or 100', in particular, expandable member 30, 130 or 130', engages tissue at a desired location or locations, such as a chamber of heart 209 or renal artery of patient 206. Catheter 10, 100 or 100' is typically connected by a suitable connector at its proximal end to console 202. Console 202 comprises a RF generator 208, which supplies high-frequency electrical energy via the catheter for ablating tissue 210 at the locations engaged by electrode 34, or 134.

Console 202 may also use magnetic position sensing to determine position coordinates of the distal end of catheter 10, 100 or 100' inside the body of the patient 206. For this purpose, a driver circuit in console 202 drives field generators to generate magnetic fields within the body of patient 206. Typically, the field generators comprise coils, which are placed below the patient's torso at known positions external to the patient. These coils generate magnetic fields in a predefined working volume that contains the area of interest. A magnetic field sensor within distal end of catheter 10, 100 or 100', generates electrical' signals in response to these magnetic fields. A signal processor in console 202 may process these signals in order to determine the position coordinates of the distal end, typically including both location and orientation coordinates. This method of position sensing is implemented in the above-mentioned CARTO system and is described in detail in U.S. Pat. Nos. 5,391,199, 6,239,724, 6,332,089, 6,484,118, 6,618,612, 6,690,963, and 7,729,742 and in PCT Patent Publication WO 96/05768, and in U.S. Patent Application Publication 2004/0068178 A1, whose disclosures are all incorporated herein by reference.

Console 202 may include system controller 212, comprising a processing unit 216 communicating with a memory 214, wherein is stored software for operation of system 200. Controller 212 may be an industry standard personal computer comprising a general purpose computer processing unit. However, in some embodiments, at least some of the functions of the controller are performed using custom designed application specific integrated circuits (ASICs) or a field programmable gate array (FPGA). Controller 212 is typically operated by the operator 204 using suitable input peripherals and a graphic user interface (GUI) 218 which enable the operator to set parameters of the system 200. GUI 218 typically also displays results of the procedure to the operator. The software in memory 214 may be downloaded to the controller in electronic form, over a network, for example. Alternatively or additionally, the software may be provided on non-transitory tangible media such as optical, magnetic or electronic storage media. In some embodiments, one or more position sensors may send signals to console 202 to provide an indication of the pressure on each of the electrodes 34, 134 of expandable element 30, 130 or 130'. Signals from wires may be provided to system controller 212 to obtain measurements from sensors. Such signals may be used to provide impedance and/or ECG readings at the location corresponding to the sensor. Similarly, signals from light sensor 46, 146 may be sent to sensor module 224 of system controller 212. Software in memory 214 may then translate the signals from light sensor 46, 146 and send a display to GUI 218 to show the operator 204 the level of contact for each of the electrodes 34, 134.

Typically, during an ablation, heat is generated by the RF energy in the tissue of the patient to effect the ablation and some of this heat is reflected to the electrode 34, 134 causing coagulation at and around the electrode. System 200 irrigates this region through irrigation apertures and the rate of flow of irrigation is controlled by irrigation module 220 and the power (RF energy) sent to electrode 34, 134 is controlled by ablation module 222. Still further, information from various sensors (not shown) may be used to determine the lesion size and depth. Details regarding this aspect may be found in U.S. patent application Ser. No. 13/113,159, entitled "Monitoring Tissue Temperature Using an Irrigated Catheter" the teachings of which is hereby incorporated by reference in its entirety. As yet another example, various sensors (not shown) may also provide intracardiac electrocardiograms to system controller 212, to be used for determining when the tissue site being ablated is no longer conducting arrhythmogenic currents.

Described herein are certain exemplary embodiments. However, one skilled in the art that pertains to the present embodiments will understand that the principles of this disclosure can be extended easily with appropriate modifications to other applications.

What is claimed is:

1. A catheter, comprising:
   an elongated body;
   an expandable element at a distal end of the elongated body;
   at least one electrode disposed on the expandable body;
   at least one contact sensor disposed on the expandable element and adjacent to the at least one electrode;
   at least one light emitting element electrically connected to the contact sensor; and
   a light sensor, the light sensor configured to receive a light signal from the at least one light emitting element.

2. The catheter of claim 1, wherein the at least one contact sensor comprises a flexible circuit.

3. The catheter of claim 2, wherein the flexible circuit is formed by sputter coating.

4. The catheter of claim 1, wherein the at least one light emitting element comprises a plurality of RGB LED, wherein each of the RGB LED corresponds to one of a plurality of electrodes.

5. The catheter of claim 1, wherein the at least one light emitting element comprises at least one white light emitting LED.

6. The catheter of claim 1, wherein the contact sensor emits a light signal to the light sensor when in a closed position.

7. The catheter of claim 1, wherein the contact sensor emits a light signal to the light sensor when in an open position.

8. The catheter of claim 1, wherein the expandable member comprises a balloon.

9. The catheter of claim 8, wherein the light sensor is operably connected to a guidewire lumen.

10. The catheter of claim 1, wherein the expandable member comprises a basket configuration having a plurality of spines.

11. The catheter of claim 10, wherein the light sensor is operably connected to a puller wire operably disposed along a central axis of the elongate body.

12. The catheter of claim 1, wherein the expandable member comprises a helical shaped member.

13. The catheter of claim 12, wherein the light sensor is operably connected to a translation member operably disposed along a central axis of the elongate body.

14. The catheter of claim 12, wherein the helical shaped member comprises a shape memory material.

15. A method for the ablation of a portion of tissue of a patient by an operator comprising:
    inserting a catheter into the patient, wherein the catheter comprises:
    an elongated body;
    an expandable element positioned at a distal end of the elongated body;
    at least one electrode disposed on the expandable body;
    at least one contact sensor disposed on the expandable element and adjacent to the at least one electrode;
    at least one light emitting element electrically connected to the contact sensor; and
    a light sensor, the light sensor configured to receive a light signal from the at least one light emitting element;
    connecting the catheter to a system controller capable of receiving signals from the light sensor and delivering power to the electrode;
    displaying an image based on the signals received from the light sensor; and
    controlling the power to the electrode to ablate tissue.

16. The method of claim 15, further comprising positioning the at least one electrode based on the displayed image based on the received light signals.

17. The method of claim 15, wherein the received signals from the light sensor comprise signals from a plurality of RGB LED.

18. The method of claim 17, wherein the expandable member is adjusted based on the displayed image.

19. The method of claim 17, further comprising estimating a degree of contact of the electrode based on the displayed image.

20. The method of claim 15, wherein the received signals from the light sensor comprise signals from a plurality of white light emitting LED.

* * * * *